United States Patent
Gui et al.

(10) Patent No.: US 10,895,552 B1
(45) Date of Patent: Jan. 19, 2021

(54) METHOD FOR PREPARING RATIOMETRIC ELECTROCHEMICAL APTASENSOR FOR VANILINE BASED ON NANOCOMPOSITE MODIFIED ELECTRODE

(71) Applicant: Qingdao University, Qingdao (CN)

(72) Inventors: Rijun Gui, Qingdao (CN); Yujiao Sun, Qingdao (CN); Hui Jin, Qingdao (CN); Xiaowen Jiang, Qingdao (CN)

(73) Assignee: QINGDAO UNIVERSITY, Qingdao (CN)

(*) Notice: Subject to any disclaimer, the term of this patent is extended or adjusted under 35 U.S.C. 154(b) by 0 days.

(21) Appl. No.: 16/618,384

(22) PCT Filed: Mar. 14, 2019

(86) PCT No.: PCT/CN2019/078076
§ 371 (c)(1),
(2) Date: May 14, 2020

(87) PCT Pub. No.: WO2020/093638
PCT Pub. Date: May 14, 2020

(30) Foreign Application Priority Data

Nov. 5, 2018 (CN) .......................... 2018 1 1307069

(51) Int. Cl.
*G01N 27/327* (2006.01)
(52) U.S. Cl.
CPC ................................ *G01N 27/3278* (2013.01)
(58) Field of Classification Search
None
See application file for complete search history.

(56) References Cited

FOREIGN PATENT DOCUMENTS

CN 105973956 A 9/2016
CN 106018806 A 10/2016
(Continued)

OTHER PUBLICATIONS

"Cu-based Metal—Organic Frameworks as a Catalyst to Construct a Ratiometric Electrochemical Aptasensor for Sensitive Lipopolysaccharide Detection", Analytical Chemistry, 87(22): p. 11345-11352, Nov. 2015.*

(Continued)

*Primary Examiner* — J. Christopher Ball
(74) *Attorney, Agent, or Firm* — Bayramoglu Law Offices LLC

(57) ABSTRACT

A method for preparing a ratiometric electrochemical aptasensor for vanillin based on an aptamer-gold nanoparticle-ferrocene-Ketjenblack-ZIF-8 nanocomposite modified electrode includes, dripping ZIF-8 nanocomposite doped with ferrocene and Ketjenblack on the surface of the bare glassy carbon electrode, and immersing this modified electrode in the chloroauric acid solution. The cyclic voltammetry is employed to scan and electrodeposit gold nanoparticles to obtain the gold nanoparticle-deposited ZIF-8 nanocomposite. The aptamer of vanillin is attached to gold nanoparticles via Au—S bonds to construct an aptamer-coupled nanocomposite sensing platform. Then, the electrochemical curves in the presence of different vanillin concentrations are measured, the linear relationship between the ratios of the current peak intensities of ferrocene and vanillin and the molar concentrations of vanillin is fitted, and the ratiometric electrochemical aptasensor for vanillin is constructed.

5 Claims, 1 Drawing Sheet

(56) References Cited

FOREIGN PATENT DOCUMENTS

| | | |
|---|---|---|
| CN | 106518895 A | 3/2017 |
| CN | 107331877 A | 11/2017 |
| CN | 109187693 A | 1/2019 |

OTHER PUBLICATIONS

"Aptamer based vanillin sensor using an ion-sensitive field-effect transistor", Microchimica Acta, 185(1): p. 3 (10 pages), Jan. 2018.*

A. T. Ezhil Vilian, et al., Fabrication of Palladium Nanoparticles on Porous Aromatic Frameworks as a Sensing Platform to Detect Vanillin, American Chemical Society Appl. Mater., May. 5, 2016, pp. 12740-12747, 8.

Kun-Yi Andrew Lin, et al., Selective generation of vanillin from catalytic oxidation of a lignin model compoud using ZIF-derived carbon-supported cobalt nanocomposite, Journal of the Taiwan Institute of Chemical Engineers, Jul. 6, 2017, pp. 337-343, 78.

Jinpeng Wang, et al., ZIF-8 Ferrocene Encapsulated: A Promising Precursor to Single-Atom Fe Embedded Nitrogen-Doped Carbon as Highly Efficient Catalyst for Oxygen Electroreduction, Advanced Science News, Small, Mar. 5, 2018, 1704282, 14.

Peihong Deng, et al., The Electrochemical Behavior and Determination of Vanillin on Electrode Modified by Graphene Functionalized with Ferroferric Oxide Nanoparticles, Journal of Hengyang Normal University, 2017, pp. 71-77, vol. 38, No. 3.

Chen Li-Xin, et al., Analysis for Vanillin in Food at Imidazole Type Carbon Ionic Liquids Modified Electrode, Modem Food Science and Technology, 2013, pp. 629-632, vol. 29, No. 3.

\* cited by examiner

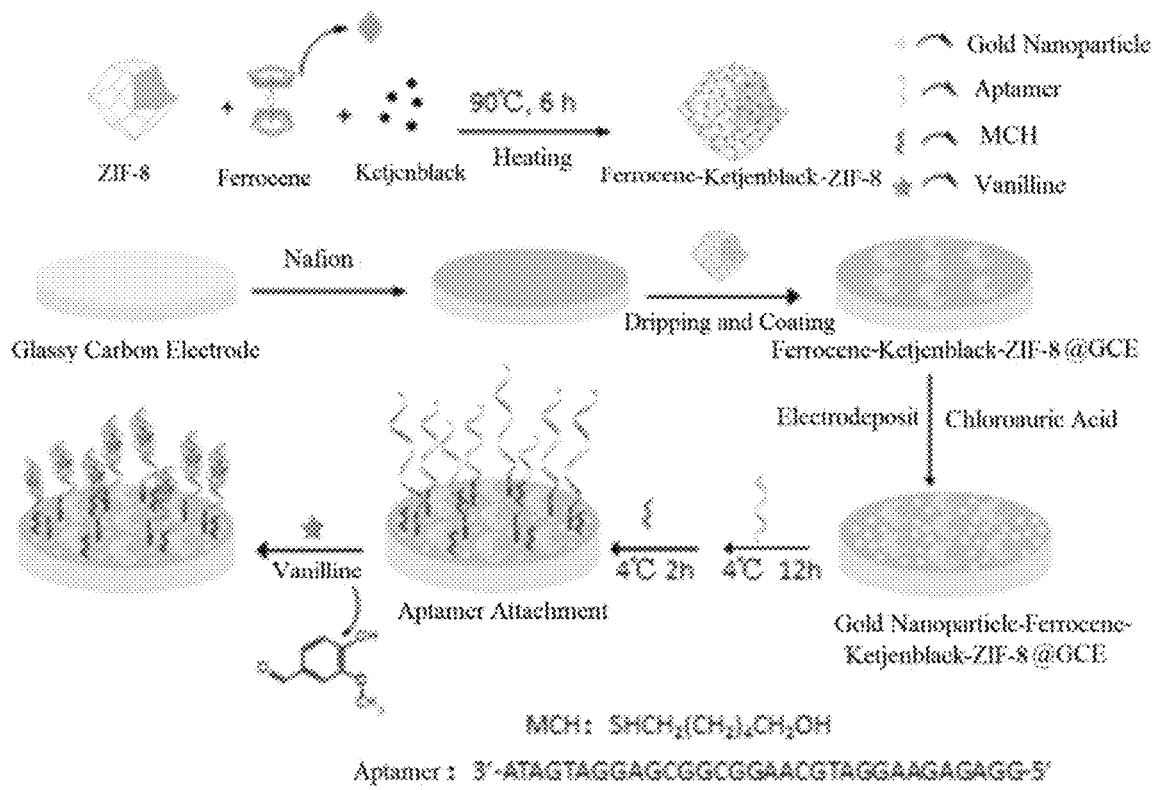
FIG. 1
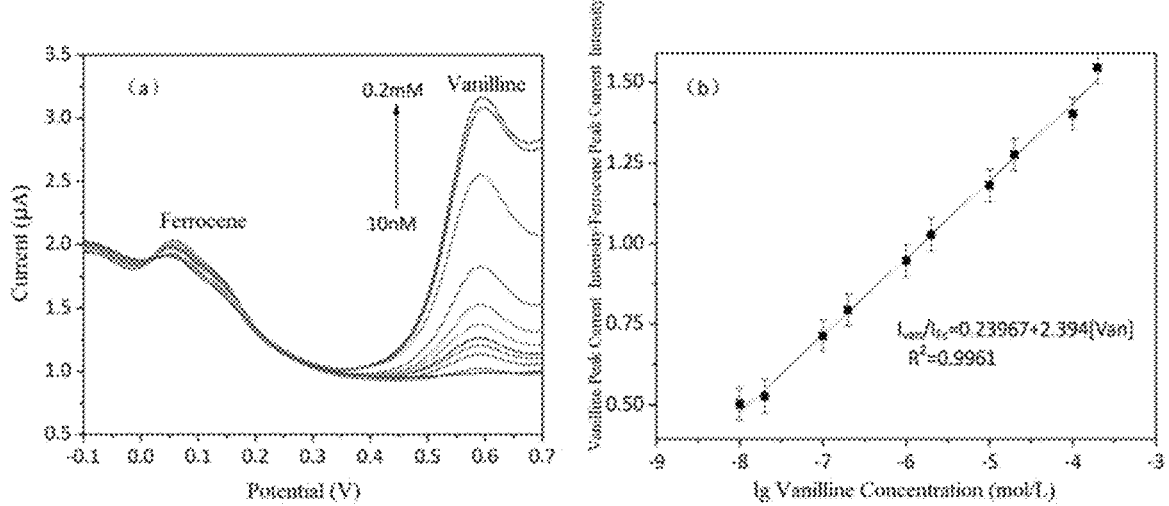
FIG. 2
FIG. 3

METHOD FOR PREPARING RATIOMETRIC ELECTROCHEMICAL APTASENSOR FOR VANILINE BASED ON NANOCOMPOSITE MODIFIED ELECTRODE

CROSS REFERENCE TO THE RELATED APPLICATIONS

This application is the national phase entry of International Application No. PCT/CN2019/078076, filed on Mar. 14, 2019, which is based upon and claims priority to Chinese Patent Application No. 201811307069.3, filed on Nov. 5, 2018, the entire contents of which are incorporated herein by reference.

TECHNICAL FIELD

The present disclosure belongs to the crossing technical field of nanocomposite and electrochemical sensor. More specifically, the present disclosure relates to a method for preparing a ratiometric electrochemical aptasensor for vanillin based on an aptamer-gold nanoparticle-ferrocene-Ketjenblack-ZIF-8 nanocomposite modified electrode, and the prepared sensor can be used to detect vanillin efficiently.

BACKGROUND

Metal-Organic Frameworks (MOFs) have the advantages of large specific surface area, high porosity, ordered crystal structure and good mechanical stability. Due to the generally poor conductivity of MOFs, the research and application of MOFs in electrochemical sensing have rarely been reported. As a zeolite-like MOFs, ZIF-8 has excellent thermal stability and chemical stability. The composite prepared by mixing ZIF-8 with electroactive materials can significantly improve the conductivity and electrochemical sensing performance of ZIF-8. Ketjenblack is a carbon black produced by a special production process. Compared with ordinary conductive carbon black, high conductivity can be achieved by adding an extremely low amount of Ketjenblack. The composite prepared by mixing Ketjenblack and ZIF-8 not only has a large specific surface area and a high porosity, but also has good electrical conductivity.

Vanillin, having a chemical formula of $C_8H_8O_3$, is a flavor component of vanilla beans, and is widely found in beets, vanilla beans, benzoin gum, balsam of Peru, tolu balsam and some other products. Vanillin is a white needle-like crystal or light yellow crystal powder with a strong aroma, which is a widely used edible spice. Vanillin is widely used in food, condiments, cosmetics, pharmaceuticals and other fields, while excessive intake of vanillin in human body can cause headaches, nausea, vomiting, kidney damage and other problems. Therefore, simple, rapid, highly sensitive and quantitative detection of vanillin is important for monitoring human health. Currently, methods for detecting vanillin mainly include high performance liquid chromatography, capillary electrophoresis, ultraviolet absorption spectroscopy, fluorescence spectroscopy, surface plasmon resonance, colorimetry, chemiluminescence, voltammetry and others methods. With the advantages of simple operation, fast signal response, low sample consumption, low cost and high sensitivity, electrochemical sensing analysis can be used for the efficient detection of vanillin.

Electrochemical detection of vanillin has been reported in the literature. Peihong Deng et al. designed an electrode modified by graphene functionalized with ferroferric oxide nanoparticles for electrochemical detection of vanillin (Electrochemical Behavior and Determination of Vanillin on Electrode Modified by Graphene Functionalized with Ferroferric Oxide Nanoparticles, Peihong Deng, Xiaopeng Liu, Quanguo He, Junhua Li, Journal of Hengyang Normal University, 2017, 3, 71-77). Lixin Chen et al. reported an ionic liquid modified carbon paste electrode for the determination of vanillin in foods (Determination of Vanillin in Foods by Ionic Liquid Modified Carbon Paste Electrode, Lixin Chen, Xintian Li, Hong Fang, Yuan Zhou, Modern Food Science and Technology, 2013, 3, 629-632). Peihong Deng et al. applied for an invention patent for the detection of vanillin in foods based on a graphene-cuprous oxide composite film modified acetylene black electrode by an electrochemical method (Graphene-Cuprous Oxide Composite Film Modified Acetylene Black Electrode and Method for Detecting Vanillin in Foods, Peihong Deng, Quanguo He, Rongying Zeng, Jun Zhang, Chinese Invention Patent. Publication No. CN105973956A).

Currently, in the electrochemical method for detecting vanillin, the interaction between electroactive substances and vanillin causes changes in electrical signal strength, thereby detecting vanillin. This method relies on a single electrochemical signal output. The single-signal detection method is susceptible to the factors including the background, reagent, system and environmental conditions, resulting in the fluctuation of the measurement results. In contrast, employing the dual-signal ratio processing to obtain the intensity ratio of the signals realizes a self-calibration function, which effectively eliminates the interference of the self-signal and the background signal and improves the accuracy and reliability of the detection results. In this regard, the present disclosure designs a ratiometric electrochemical aptasensor for vanillin based on an aptamer-gold nanoparticle-ferrocene-Ketjenblack-ZIF-8 nanocomposite modified electrode. This novel electrochemical sensor can be used to detect vanillin efficiently. So far, detecting vanillin by using a ratiometric electrochemical aptasensor or the ratiometric electrochemical aptasensor based on the aptamer-gold nanoparticle-ferrocene-Ketjenblack-ZIF-8 nanocomposite modified electrode has not yet been reported in domestic and foreign literature and patents.

SUMMARY

The objective of the present disclosure is to overcome the deficiencies of the prior art described above, and to provide a method for preparing a ratiometric electrochemical aptasensor for vanillin based on an aptamer-gold nanoparticle-ferrocene-Ketjenblack-ZIF-8 nanocomposite modified electrode, where the method is simple, low-cost and has high-sensitivity.

In order to achieve the aforementioned objective, according to the present disclosure, a process of preparing the ratiometric electrochemical aptasensor for vanillin based on the aptamer-gold nanoparticle-ferrocene-Ketjenblack-ZIF-8 nanocomposite modified electrode includes the following steps.

(1) Dissolving 2-methylimidazole (Hmim) in ethanol, adding ferrocene and Ketjenblack, stirring well to form a homogenous mixture, adding zinc nitrate, stirring evenly and then transferring to a high-pressure reactor. The reaction is continuously carried out for a period of time at a set temperature, and the product is centrifuged, washed with ethanol and dried in a vacuum to obtain a ferrocene-Ketjenblack-ZIF-8 nanocomposite.

(2) Dripping a cross-linking agent Nafion on a surface of a polished bare glassy carbon electrode, and then dripping and coating the ferrocene-Ketjenblack-ZIF-8 nanocomposite to form a ferrocene-Ketjenblack-ZIF-8 nanocomposite modified glassy carbon electrode; immersing the ferrocene-Ketjenblack-ZIF-8 nanocomposite modified glassy carbon electrode in a buffer electrolyte solution and adding chloroauric acid. In a set potential range, the cyclic voltammetry is used to scan to generate gold nanoparticles in situ by one-step electrodeposition, thereby obtaining a gold nanoparticle-deposited ZIF-8 nanocomposite.

(3) Adding aptamer DNA of vanillin with a sulfydryl terminal on the surface of the gold nanoparticle-deposited ZIF-8 nanocomposite and incubating for a period of time at 4° C. to obtain an aptamer modified gold nanoparticle-ferrocene-Ketjenblack-ZIF-8 nanocomposite modified electrode.

(4) Using the modified electrode obtained from step (3) as a working electrode, and measuring the electrochemical square-wave voltammetry curves in the presence of different vanillin concentrations; taking current peak intensities of ferrocene and vanillin as a reference signal and a response signal, respectively; fitting a linear relationship between ratios ($I_{response\ signal}/I_{reference\ signal}$) of the two current peak intensities and molar concentrations of vanillin and constructing the ratiometric electrochemical aptasensor for vanillin.

In step (1), the reaction temperature is 50-150° C., the reaction time is 3-12 h, and the mass concentration ratio of Hmim, ferrocene, Ketjenblack to zinc nitrate is (100-200):(100-500):(1-10):(50-100).

In step (2), the dosage of the Nafion is 1-10 uL, the mass concentration of the ZIF-8 nanocomposite is 1-10 mg/mL, the concentration of the chloroauric acid is 0.1-1 μmol/L, the potential range where the cyclic voltammetry is used to scan is −0.1-1.5 V, the scanning rate is 10-100 mVs$^{-1}$, and the scanning number is 5-30 cycles.

In step (3), the concentration of the aptamer of vanillin is 1-10 μmol/L and the incubation time is 12-48 h.

In step (4), the linear detection range of vanillin concentration is 0.01-500 μmol/L and the detection limit is 1-10 nmol/L.

The effects of the present disclosure are as follows. The ZIF-8 nanocomposite doped with ferrocene and Ketjenblack is dripped and coated on the surface of the glassy carbon electrode and this modified electrode is immersed in the chloroauric acid solution as the working electrode. The cyclic voltammetry is used to scan and electrodeposit gold nanoparticles to obtain the gold nanoparticle-ferrocene-Ketjenblack-ZIF-8 nanocomposite modified electrode. The aptamer of vanillin is attached to gold nanoparticles via Au—S bonds to construct an aptamer-coupled ZIF-8 nanocomposite sensing platform. Then, the ratios of the current peak intensities of vanillin to ferrocene in the presence of different vanillin concentrations are measured, the linear relationship between the different ratios and the corresponding concentrations of vanillin is fitted, and the ratiometric electrochemical aptasensor for vanillin is constructed. Compared with the prior art, the method of the present disclosure has simple operations and low cost, where raw materials are easy to obtain, the product has high electrochemical activity, and the ratiometric signal has a strong anti-interference ability. The method has high sensitivity and good accuracy, which can be developed into a novel ratiometric electrochemical aptasensor for the efficient detection of vanillin.

BRIEF DESCRIPTION OF THE DRAWINGS

FIG. 1 is a schematic diagram showing the preparation for the ratiometric electrochemical aptasensor for vanillin based on aptamer-gold nanoparticle-ferrocene-Ketjenblack-ZIF-8 nanocomposite modified electrode and the detection for vanillin;

FIG. 2 is a diagram showing electrochemical square-wave voltammetry curves in the presence of different vanillin concentrations determined by using the ratiometric electrochemical aptasensor of the present disclosure;

FIG. 3 shows the linear relationship fitted between the ratios of oxidation current peak intensities of vanillin and ferrocene and different vanillin concentrations.

DETAILED DESCRIPTION OF THE EMBODIMENTS

The present disclosure will be further described in detail below in conjunction with the drawings and specific embodiments.

Embodiment 1

This embodiment relates to the preparation for the ratiometric electrochemical aptasensor for vanillin based on an aptamer-gold nanoparticle-ferrocene-Ketjenblack-ZIF-8 nanocomposite modified electrode and the ratiometric electrochemical detection for vanillin. The preparation process and the principle of the ratiometric electrochemical aptasensor are shown in FIG. 1, and the specific process steps are as follows.

2-methylimidazole (Hmim) is dissolved in ethanol. Ferrocene and Ketjenblack are added for stirring well to obtain the homogenous mixture, and then zinc nitrate is added for stirring evenly and then being transferred to a high-pressure reactor, wherein the mass concentration ratio of Hmim, ferrocene, Ketjenblack, to zinc nitrate is 130:200:1:60. The reaction is continuously carried out at 90° C. for 6 h, and the product is centrifuged, washed with ethanol, and dried in a vacuum to obtain a ferrocene-Ketjenblack-ZIF-8 nanocomposite.

2 uL of cross-linking agent Nafion is dripped on a surface of a polished bare glassy carbon electrode, and then the ferrocene-Ketjenblack-ZIF-8 nanocomposite with a concentration of 2 mg/mL is dripped and coated to form a ferrocene-Ketjenblack-ZIF-8 nanocomposite modified glassy carbon electrode. The electrode is immersed in a buffer electrolyte solution, and chloroauric acid is added to adjust the concentration to 0.2 μmol/L. In the potential range of −0.1-0.7 V, the cyclic voltammetry is used to scan for 10 cycles at a scanning rate of 20 mVs$^{-1}$ to generate gold nanoparticles in situ by one-step electrodeposition, thereby obtaining a gold nanoparticle-deposited ZIF-8 nanocomposite.

Aptamer DNA of vanillin with a sulfydryl terminal whose concentration is 2 μmol/L is dripped on the surface of the gold nanoparticle-deposited ZIF-8 nanocomposite, and then incubated for 12 h at 4° C. to obtain an aptamer modified gold nanoparticle-ferrocene-Ketjenblack-ZIF-8 nanocomposite modified electrode. The modified electrode is used as the working electrode, and the electrochemical square-wave voltammetry curves in the presence of different vanillin concentrations are measured. Taking the current peak intensities of ferrocene and vanillin as a reference signal and a response signal, respectively, the linear relationship between the ratios ($I_{response\ signal}/I_{reference\ signal}$) of the two current peak intensities and the molar concentrations of vanillin is fitted, and the ratiometric electrochemical aptasensor for vanillin is constructed. As shown in FIG. 2 and FIG. 3, the linear detection range of the vanillin concentration is 0.01-200 µmol/L and the detection limit is 3 nmol/L.

Embodiment 2

This embodiment relates to the preparation for the ratiometric electrochemical aptasensor for vanillin based on a nanocomposite modified electrode and the ratiometric electrochemical detection for vanillin. The schematic diagram of the preparation process and the principle is the same as embodiment 1, and the specific process steps are as follows.

2-methylimidazole (Hmim) is dissolved in ethanol. Ferrocene and Ketjenblack are added for stirring well to obtain the homogenous mixture, and then zinc nitrate is added for stirring evenly and then being transferred to a high-pressure reactor, wherein the mass concentration ratio of Hmim, ferrocene, Ketjenblack, to zinc nitrate is 150:300:2:80. The reaction is continuously carried out at 120° C. for 12 h, and the product is centrifuged, washed with ethanol, and dried in a vacuum to obtain a ferrocene-Ketjenblack-ZIF-8 nanocomposite.

5 uL of cross-linking agent Nafion is dripped on a surface of a polished bare glassy carbon electrode, and then the ferrocene-Ketjenblack-ZIF-8 nanocomposite with a concentration of 5 mg/mL is dripped and coated to form a ferrocene-Ketjenblack-ZIF-8 nanocomposite modified glassy carbon electrode. The ferrocene-Ketjenblack-ZIF-8 nanocomposite modified glassy carbon electrode is immersed in a buffer electrolyte solution, and chloroauric acid is added to adjust the concentration to 0.5 µmol/L. In the potential range of −0.2-1.0 V, the cyclic voltammetry is used to scan for 20 cycles at a scanning rate of 40 mVs$^{-1}$ to generate gold nanoparticles in situ by one-step electrodeposition, thereby obtaining a gold nanoparticle-deposited ZIF-8 nanocomposite.

Aptamer DNA of vanillin with a sulfydryl terminal whose concentration is 4 µmol/L on the surface of the gold nanoparticle-deposited ZIF-8 nanocomposite, and then incubated for 24 h at 4° C. to obtain an aptamer modified gold nanoparticle-ferrocene-Ketjenblack-ZIF-8 nanocomposite modified electrode. The modified electrode is used as the working electrode, and the electrochemical square-wave voltammetry curves in the presence of different vanillin concentrations are measured. Taking the current peak intensities of ferrocene and vanillin as a reference signal and a response signal, respectively, the linear relationship between the ratios ($I_{response\ signal}/I_{reference\ signal}$) of the two current peak intensities and the molar concentrations of vanillin is fitted, and the ratiometric electrochemical aptasensor for vanillin is constructed. The linear detection range of the vanillin concentration is 0.05-300 µmol/L and the detection limit is 5 nmol/L.

Embodiment 3

This embodiment relates to the preparation for the ratiometric electrochemical aptasensor for vanillin based on a nanocomposite modified electrode and the ratiometric electrochemical detection for vanillin. The schematic diagram of the preparation process and the principle is the same as embodiment 1, and the specific process steps are as follows.

2-methylimidazole (Hmim) is dissolved in ethanol. Ferrocene and Ketjenblack are added for stirring well to obtain the homogenous mixture, and then zinc nitrate is added for stirring evenly and then being transferred to a high-pressure reactor, wherein the mass concentration ratio of Hmim, ferrocene, Ketjenblack, to zinc nitrate is 200:400:3:100. The reaction is continuously carried out at 150° C. for 8 h, and the product is centrifuged, washed with ethanol, and dried in a vacuum to obtain a ferrocene-Ketjenblack-ZIF-8 nanocomposite.

8 uL of cross-linking agent Nafion is dripped on a surface of a polished bare glassy carbon electrode, and then the ferrocene-Ketjenblack-ZIF-8 nanocomposite with a concentration of 6 mg/mL is dripped and coated to form a ferrocene-Ketjenblack-ZIF-8 nanocomposite modified glassy carbon electrode. The ferrocene-Ketjenblack-ZIF-8 nanocomposite modified glassy carbon electrode is immersed in a buffer electrolyte solution, and chloroauric acid is added to adjust the concentration to 0.8 µmol/L. In the potential range of −0.5-1.5 V, the cyclic voltammetry is used to scan for 30 cycles at a scanning rate of 50 mVs$^{-1}$ to generate gold nanoparticles in situ by one-step electrodeposition, thereby obtaining a gold nanoparticle-deposited ZIF-8 nanocomposite.

Aptamer DNA of vanillin with a sulfydryl terminal whose concentration is 5 µmol/L is dripped on the surface of the gold nanoparticle-deposited ZIF-8 nanocomposite, and then incubated for 36 h at 4° C. to obtain an aptamer modified gold nanoparticle-ferrocene-Ketjenblack-ZIF-8 nanocomposite modified electrode. The modified electrode is used as the working electrode, and the electrochemical square-wave voltammetry curves in the presence of different vanillin concentrations are measured. Taking the current peak intensities of ferrocene and vanillin as a reference signal and a response signal, respectively, the linear relationship between the ratios ($I_{response\ signal}/I_{reference\ signal}$) of the two current peak intensities and the molar concentrations of vanillin is fitted, and the ratiometric electrochemical aptasensor for vanillin is constructed. The linear detection range of the vanillin concentration is 0.1-500 µmol/L and the detection limit is 10 nmol/L.

The above descriptions are only some preferred embodiments of the present disclosure. It should be noted that those skilled in the art can also make several improvements and modifications without departing from the principles of the present disclosure, and these improvements and modifications shall still fall within the protective scope of the present disclosure.

What is claimed is:

1. A method for preparing a ratiometric electrochemical aptasensor for vanillin based on an aptamer-gold nanoparticle-ferrocene-Ketjenblack-ZIF-8 nanocomposite modified electrode, comprising the following steps:
    (1) dissolving 2-methylimidazole (Hmim) in ethanol, adding ferrocene and Ketjenblack, stirring to obtain a homogenous mixture, adding zinc nitrate to the homogenous mixture and stirring evenly to obtain a first solution, and then transferring the first solution to a high-pressure reactor; wherein a reaction in the first solution is continuously carried out for a period of time at a set temperature to obtain a product, and the product is centrifuged, washed with ethanol, and dried in a vacuum to obtain a ferrocene-Ketjenblack-ZIF-8 nanocomposite;
    (2) dripping a cross-linking agent Nafion on a surface of a polished bare glassy carbon electrode, and then dripping and coating the ferrocene-Ketjenblack-ZIF-8 nanocomposite on a surface of the cross-linking agent Nafion to form a ferrocene-Ketjenblack-ZIF-8 nanocomposite modified glassy carbon electrode; immersing the ferrocene-Ketjenblack-ZIF-8 nanocomposite modified glassy carbon electrode in a buffer electrolyte solution, adding chloroauric acid to the buffer electrolyte solution to obtain a second solution; and then in a set potential range, employing cyclic voltammetry to scan the second solution and generate gold nanoparticles in situ by one-step electrodeposition, thereby obtaining a gold nanoparticle-deposited ZIF-8 nanocomposite;

(3) adding aptamer DNA of the vanillin with a sulfydryl terminal on a surface of the gold nanoparticle-deposited ZIF-8 nanocomposite, and incubating for a period of time at 4° C. to obtain an aptamer modified gold nanoparticle-ferrocene-Ketjenblack-ZIF-8 nanocomposite modified electrode;

(4) using the aptamer modified gold nanoparticle-ferrocene-Ketjenblack-ZIF-8 nanocomposite modified electrode obtained from the step (3) as a working electrode, and measuring electrochemical square-wave voltammetry curves in the presence of different vanillin concentrations; taking current peak intensities of the ferrocene and the vanillin as a reference signal and a response signal, respectively, fitting a linear relationship between ratios $I_{response\ signal}/I_{reference\ signal}$ of the current peak intensities of the ferrocene and the vanillin and molar concentrations of the vanillin, and constructing the ratiometric electrochemical aptasensor for the vanillin.

2. The method for preparing the ratiometric electrochemical aptasensor for the vanillin based on the aptamer-gold nanoparticle-ferrocene-Ketjenblack-ZIF-8 nanocomposite modified electrode according to claim 1, wherein, in the step (1), a reaction temperature is 50-150° C., a reaction time is 3-12 h, and a mass concentration ratio of the Hmim, the ferrocene, the Ketjenblack, to the zinc nitrate is (100-200):(100-500):(1-10):(50-100).

3. The method for preparing the ratiometric electrochemical aptasensor for the vanillin based on the aptamer-gold nanoparticle-ferrocene-Ketjenblack-ZIF-8 nanocomposite modified electrode according to claim 1, wherein, in the step (2), a dosage of the Nafion is 1-10 uL, a mass concentration of the ZIF-8 nanocomposite is 1-10 mg/mL, a molar concentration of the chloroauric acid is 0.1-1 μmol/L, a potential range where the cyclic voltammetry is used to scan is −0.1-1.5 V, a scanning rate of the cyclic voltammetry is 10-100 mVs$^{-1}$, and a scanning number of the cyclic voltammetry is 5-30 cycles.

4. The method for preparing the ratiometric electrochemical aptasensor for vanillin based on the aptamer-gold nanoparticle-ferrocene-Ketjenblack-ZIF-8 nanocomposite modified electrode according to claim 1, wherein, in the step (3), a molar concentration of the aptamer of the vanillin is 1-10 μmol/L, and an incubation time is 12-48 h.

5. The method for preparing the ratiometric electrochemical aptasensor for the vanillin based on the aptamer-gold nanoparticle-ferrocene-Ketjenblack-ZIF-8 nanocomposite modified electrode according to claim 1, wherein, in the step (4), a linear detection range of the different vanillin concentration is 0.01-500 μmol/L, and a detection limit of the vanillin is 1-10 nmol/L.

* * * * *